(12) United States Patent
Rotherham et al.

(10) Patent No.: US 9,176,134 B2
(45) Date of Patent: Nov. 3, 2015

(54) DIAGNOSIS OF TUBERCULOSIS

(71) Applicant: CSIR, Pretoria (ZA)

(72) Inventors: Lia Suzanne Rotherham, Pretoria (ZA); Makobetse Abel Khati, Pretoria (ZA); Matsopiane Charlotte Maserumule, Pretoria (ZA)

(73) Assignee: CSIR, Pretoria (ZA)

( * ) Notice: Subject to any disclaimer, the term of this patent is extended or adjusted under 35 U.S.C. 154(b) by 0 days.

(21) Appl. No.: 14/346,398

(22) PCT Filed: Sep. 21, 2012

(86) PCT No.: PCT/IB2012/055025
§ 371 (c)(1),
(2) Date: Mar. 21, 2014

(87) PCT Pub. No.: WO2013/042077
PCT Pub. Date: Mar. 28, 2013

(65) Prior Publication Data
US 2014/0370516 A1      Dec. 18, 2014

(30) Foreign Application Priority Data

Sep. 23, 2011   (ZA) ................................. 2011/06987
Jun. 8, 2012    (ZA) ................................. 2012/04226

(51) Int. Cl.
*C12N 15/115*    (2010.01)
*G01N 33/569*    (2006.01)
*C12Q 1/68*      (2006.01)
*G01N 33/53*     (2006.01)

(52) U.S. Cl.
CPC .......... *G01N 33/5695* (2013.01); *C12Q 1/6883* (2013.01); *G01N 33/5308* (2013.01)

(58) Field of Classification Search
None
See application file for complete search history.

(56) References Cited

FOREIGN PATENT DOCUMENTS

WO    WO2009/027507    3/2009
WO    WO2010/144799   12/2010

OTHER PUBLICATIONS

Qin, Lianhua et al., "The selection and application of ssDNA aptamers against MPT64 protein in Mycobacterium tuberculosis", Clin Chem Lab Med 2009, 47(4):405-411.
Rotherham, New diagnostic and therapeutic tools for tuberculosis using anti-ESAT-6/CFP-10 Aptamers, Jan. 1, 2008, http://researchspace.csir.co.za/dspace/hande/10204/2700 [retrieved Mar. 21, 2014].
Bannantine et al., Development and characterization of monoclonal antibodies and aptamers against major antigens of Mycobacterium avium subsp. Paratuberculosis, Clinical and Vaccine Immunology, 14(5):518-526, 2007.
Chen et al., Aptamer from whole-bacterium SELEX as new therapeutic reagent against virulent Mycobacterium tuberculosis, Biochemical and Biophysical Research Communications, 357(3):743-748, 2007.
Renshaw et al., Conclusive evidence that the major T-cell antigens of the Mycobacterium tuberculosis complex ESAT-6 and CFP-10 form a tight, 1:1 complex and characterization of the structural properties of ESAT-6, CFP-10 and the ESAT-6CFP-10 complex. Implications for pathogenesis and virulence, J. Biol. Chem., 277(24):21598-21603, 2002.
Rotherham et al., Selection and Application of ssDNA aptamers to detect active TB from sputum samples, PLOS One, 7(10):e46862, 2012.

*Primary Examiner* — Tracy Vivlemore
(74) *Attorney, Agent, or Firm* — McCarter & English, LLP; Jill Mello; Marcie B. Clarke

(57) ABSTRACT

The invention comprises an oligonucleotide selected from the group comprising SEQ ID NO: 1, SEQ ID NO: 2, SEQ ID NO: 3; SEQ ID NO: 4; SEQ ID NO: 5 and SEQ ID NO: 6. The invention also comprises a complementary oligonucleotide of the oligonucleotide selected from the group comprising SEQ ID NO: 1, SEQ ID NO: 2, SEQ ID NO: 3; SEQ ID NO: 4; SEQ ID NO: 5 and SEQ ID NO: 6, an oligonucleotide being at least 80% homologous thereto, a truncated portion of any of the aforementioned, or a pairing of any of the aforementioned.

14 Claims, 12 Drawing Sheets

SEQUENCE LISTING

```
<160> NUMBER OF SEQ ID NOS: 6

<210> SEQ ID NO 1
<211> LENGTH: 90
<212> TYPE: DNA
<213> ORGANISM: Escherichia coli

<400> SEQUENCE: 1
gcctgttgtg agcctcctaa cccgtctaac gagattgggt cttcatatgg ctcgaagcgc      60
gcggtcagtt catgcttatt cttgtctccc                                       90

<210> SEQ ID NO 2
<211> LENGTH: 90
<212> TYPE: DNA
<213> ORGANISM: Escherichia coli

<400> SEQUENCE: 2
```

```
gcctgttgtg agcctcctaa ctccggtctt caacatgtcc aatcgaactt cggcggaaat      60
cctttacctg catgcttatt cttgtctccc                                      90

<210> SEQ ID NO 3
<211> LENGTH: 90
<212> TYPE: DNA
<213> ORGANISM: Escherichia coli

<400> SEQUENCE: 3
gcctgttgtg agcctcctaa ccccatctta tacgtatatg gactcatctc gaccccgat      60 aggcttggta catgcttatt cttgtctccc                                      90

<210> SEQ ID NO 4
<211> LENGTH: 90
<212> TYPE: DNA
<213> ORGANISM: Escherichia coli

<400> SEQUENCE: 4
gcctgttgtg agcctcctaa ctaatgtgga tgctgcatcg ttagtatttc tagcatgcaa      60
tataggcatg catgcttatt cttgtctccc                                      90

<210> SEQ ID NO 5
<211> LENGTH: 89
<212> TYPE: DNA
<213> ORGANISM: Escherichia coli

<400> SEQUENCE: 5
gcctgttgtg agcctcctaa cttccaataa cgatacttaa acctggtctt tgccagtcaa      60
tgatagcatc atgcttattc ttgtctccc                                       89

<210> SEQ ID NO 6
<211> LENGTH: 90
<212> TYPE: DNA
<213> ORGANISM: Escherichia coli

<400> SEQUENCE: 6
gcctgttgtg agcctcctaa cacacacgta gcgccttgtt gaagtatact caaagcattc      60
tccacgcggg catgcttatt cttgtctccc                                      90
```

DIAGNOSIS OF TUBERCULOSIS

RELATED APPLICATIONS

This application is a 35 U.S.C. §371 national stage filing of International Application No. PCT/IB2012/055025, filed Sep. 21, 2012, which claims priority to South African Patent Application No. 2011/06987, filed Sep. 23, 2011 and South African Patent Application No. 2012/04226, filed Jun. 8, 2012. The entire contents of the foregoing applications are hereby incorporated by reference.

THIS INVENTION relates to the diagnosis of tuberculosis (TB). More particularly, the invention relates to an oligonucleotide that can be used in the diagnosis of TB, to an in vitro method of diagnosing TB, and to a diagnostic kit for diagnosing TB.

Tuberculosis (TB) is one of the biggest killers among infectious diseases, despite the worldwide use of a live attenuated vaccine and several antibiotics. There are an estimated eight million new cases per year and two million deaths annually, which are compounded by the emergence of drug resistance TB and co-infections with HIV.

Despite the enormous burden of TB, conventional approaches to diagnosis currently used continue to rely on tests that have major drawbacks. Many of these tests are slow and lack both sensitivity and specificity or require expensive equipment and trained personnel. For example, sputum smear microscopy is insensitive; the culture method is technically complex and slow; chest radiography is non-specific, and the tuberculin skin test is imprecise, and its results are non-specific; nucleic acid amplification tests and phage display are rapid but specificity and sensitivity are low. The recently discovered nucleic acid amplification test called the GeneXpert-, addresses the problems of time and sensitivity but the machine required is extremely expensive.

It is accordingly an object of this invention to provide an improved method of diagnosing TB, with the method being more sensitive and/or more specific than those of which the Applicant is aware.

According to a first aspect of the invention, there is provided an oligonucleotide selected from the group comprising SEQ ID NO: 1, SEQ ID NO: 2, SEQ ID NO: 3, SEQ ID NO: 4, SEQ ID NO: 5 and SEQ ID NO: 6, a complementary oligonucleotide thereof, an oligonucleotide being at least 80% homologous thereto, a truncated portion of any of the aforementioned, or a pairing of any of the aforementioned.

More specifically, this aspect of the invention may comprise
(i) an oligonucleotide selected from the group comprising SEQ ID NO: 1, SEQ ID NO: 2, SEQ ID NO: 3, SEQ ID NO: 4, SEQ ID NO: 5, and SEQ ID NO: 6; and/or
(ii) a complementary oligonucleotide of an oligonucleotide selected from the group comprising SEQ ID NO: 1, SEQ ID NO: 2, SEQ ID NO: 3, SEQ ID NO: 4, SEQ ID NO: 5, and SEQ ID NO: 6; and/or
(iii) an oligonucleotide being at least 80% homologous to an oligonucleotide selected from the group comprising SEQ ID NO: 1, SEQ ID NO: 2, SEQ ID NO: 3, SEQ ID NO: 4, SEQ ID NO: 5, and SEQ ID NO: 6; and/or
(iv) a truncated portion of an oligonucleotide selected from the group comprising SEQ ID NO: 1, SEQ ID NO: 2, SEQ ID NO: 3, SEQ ID NO: 4, SEQ ID NO: 5, and SEQ ID NO: 6; and/or
(v) a pairing of any two oligonucleotides selected from the group comprising SEQ ID NO: 1, SEQ ID NO: 2, SEQ ID NO: 3, SEQ ID NO: 4, SEQ ID NO: 5, and SEQ ID NO: 6

SEQ ID NO: 1 to SEQ ID NO: 6 are as set out hereinafter, particularly in Table 1, and in the sequence listing annexed hereto.

The oligonucleotide may be a single stranded oligonucleotide or it may be a double stranded oligonucleotide. In the preferred embodiment, the oligonucleotide is a single stranded oligonucleotide.

The oligonucleotide may be an aptamer, a truncated portion of an aptamer, or a pairing thereof, that binds specifically to a CFP-10.ESAT-6 heterodimer of a *Mycobacterium* strain. The aptamer may instead bind to a CFP-10 monomer of a *Mycobacterium* strain. More specifically, the aptamer may bind to the CFP-10.ESAT-6 heterodimer or CFP-10 monomer of the *Mycobacterium tuberculosis* (M.tb) strain.

By "a pairing thereof" is meant a pairing of two aptamers or a pairing of two truncated portions of aptamers or a pairing of an aptamer with a truncated portion of an aptamer; preferably, however, it refers to a pairing of two aptamers.

The CFP-10.ESAT-6 heterodimer and the CFP-10 monomer are early markers of active tuberculosis (TB). Aptamers are artificial nucleic acid or nucleotide ligands that can bind any molecular or cellular target of interest with high affinity and specificity. Thus, in the present invention, it was surprisingly found that more sensitive and specific diagnosis of TB can be achieved by means of aptamers, truncated portions of aptamers or pairings thereof that bind specifically to the CFP-10.ESAT-6 heterodimer and the CFP-10 monomer.

According to a second aspect of the invention, there is provided an oligonucleotide which is an aptamer, a truncated portion of an aptamer, or a pairing thereof, that binds to a CFP-10.ESAT-6 heterodimer or to a CFP-10 monomer of a *Mycobacterium* strain.

This oligonucleotide may be selected from the group comprising SEQ ID NO: 1, SEQ ID NO: 2, SEQ ID NO: 3; SEQ ID NO: 4; SEQ ID NO: 5 and SEQ ID NO: 6, a complementary oligonucleotide thereof, an oligonucleotide being at least 80% homologous thereto, a truncated portion of any of the aforementioned, or a pairing of any of the aforementioned.

In accordance with a third aspect of the invention, there is provided an in vitro method of diagnosing tuberculosis (TB), said method comprising:
(a) contacting a sample taken from an individual suspected to be infected with TB with the oligonucleotide according to the first or second aspects of the invention in a CFP-10.ESAT-6 heterodimer binding assay; and
(b) determining whether or not the oligonucleotide has bound to a CFP-10.ESAT-6 heterodimer in the sample, with binding of the oligonucleotide to the CFP-10.ESAT-6 heterodimer thus confirming the presence of the CFP-10.ESAT-6 heterodimer, and hence TB infection in the sample.

In accordance with a fourth aspect of the invention, there is provided an in vitro method of diagnosing tuberculosis (TB), said method comprising:
(a) contacting a sample taken from an individual suspected to be infected with TB with the oligonucleotide according to the first or second aspects of the invention in a CFP-10 monomer binding assay; and
(b) determining whether or not the oligonucleotide has bound to a CFP-10 monomer in the sample, with binding of the oligonucleotide to the CFP-10 monomer thus confirming the presence of the CFP-10 monomer, and hence TB infection in the sample.

In accordance with a fifth aspect of the invention, there is provided a nucleic acid comprising an oligonucleotide sequence selected from SEQ. ID. NO: 1, SEQ ID NO: 2, SEQ ID NO: 3; SEQ ID NO: 4; SEQ ID NO: 5 and SEQ ID NO: 6, a complementary oligonucleotide thereof, an oligonucleotide being at least 80% homologous thereto, a truncated portion of any of the aforementioned, or a pairing of any of the aforementioned.

It will be appreciated by a person skilled in the art of this invention that the binding assays may be chemiluminescent assays. In a preferred embodiment, the assay is a modified ELISA-type assay wherein the antibodies against a test molecule (CFP-10.ESAT-6 heterodimer or CFP-10 monomer) are replaced with a labelled aptamer of the invention, a truncated portion thereof or a pairing thereof.

In accordance with a sixth aspect of the invention, there is provided a diagnostic kit for diagnosing tuberculosis (TB), said kit including:
(a) a device for taking a sample from an individual suspect to be infected with TB; and
(b) apparatus for applying the method of diagnosing TB according to the third or fourth aspects of the invention; and
(c) optionally, a positive control and/or a negative control.

It has been found that rational truncation of the original oligonucleotide/aptamer sequences yield shorter, lower cost molecules that show comparable activity to the original parent sequences. The truncated versions of the oligonucleotide/aptamers retain those parts of the original (parent) oligonucleotide/aptamers which are predicted to play a role in target-binding. The truncated aptamers show binding to target proteins, with affinities comparable to those of the parent sequences.

It has also been found that the original full length oligonucleotides can be used in pairs for further use in a diagnostic setting.

The invention will now be described in more detail with reference to and as illustrated in the following non-limiting examples and accompanying drawings.

Hereinafter, the aptamers selected from the group comprising SEQ ID NO: 1, SEQ ID NO: 2, SEQ ID NO: 3; SEQ ID NO: 4; SEQ ID NO: 5 and SEQ ID NO: 6, are also referred to as CSIR 2.2, CSIR2.9, CSIR2.11, CSIR2.15, CSIR2.19 and CSIR2.21 respectively.

In the drawings:

FIG. 1 shows neighbour joining tree for the aptamer sequences;

FIG. 2 is a graphical representation of the 24 ssDNA aptamers (CSIR 2.1 to CSIR 2.24) that significantly (p<0.05) bound the CFP-10.ESAT-6 M. tb target protein. Statistical significant was determined by a two tailed Student t-test and the error bars denote standard deviations of experiments done in triplicate. Each aptamer was tested for binding at least twice, in independent experiments;

FIG. 3 shows binding of anti-CFP-10.ESAT-6 biotinylated ssDNA aptamers to the CFP-10.ESAT-6 heterodimer in the presence (grey shaded bar graphs) or absence (line hatched bar graphs) of anti-ESAT-6 monoclonal antibody. Error bars denote standard deviation of triplicates. Each aptamer was tested in two independent assays;

FIG. 4 shows binding of the anti-CFP-10.ESAT-6 ssDNA aptamers to ESAT-6, CFP-10, CFP-10.ESAT-6 heterodimer, EsxGH heterodimer and HIV-1 gp120, respectively, to determine specificity. Error bars show standard deviations of experiments done in triplicates;

FIG. 5 shows binding of the solid phase synthesised ssDNA aptamers to CFP-10.ESAT-6 heterodimer, CFP-10 and ESAT-6 monomers, respectively. Error bars denote standard deviation of triplicates. Each aptamer was tested in two independent assays;

FIG. 6 shows a specificity test for CSIR 2.11 aptamer. The specificity was done using lysates from bacterial cultures of the auxotroph strain of M. tb. M. smegmatis, Pseudomonas, and Streptococcus. Based on a standard curve run on the plate the cut off was determined to be $OD_{450}$=0.2, with a 99% confidence interval. Error bars denote standard deviation of triplicates. Each aptamer was tested in two independent assays;

FIG. 7 illustrates kinetic studies of 5 of the best aptamers. CFP-10 attached to a CM5 chip was used to capture the respective anti-CFP-10.ESAT-6 aptamers. The respective aptamers were injected at different concentrations at a flow rate of 10 µl/min for 5 minutes and allowed to dissociate for 10 minutes;

FIG. 8 shows folded versus unfolded aptamer binding. One batch of CSIR 2.11 was refolded and the other was used directly after thawing. The refolding step is not necessary for the binding of the aptamer to the target antigens. Thus, no significant difference was seen between the folded and the unfolded aptamer. Error bars denote standard deviation of triplicates. Each aptamer was tested in two independent assays;

FIG. 9 illustrates serial dilutions of CFP-10 on a 96 well micro-titre plate. The limit of detection for 150 nM of CSIR 2.11 is 31 ng of CFP-10 M. tb protein, with an $R^2$ of 0.85. Error bars denote standard deviation of triplicates. Each aptamer was tested in two independent assays;

FIG. 10 shows the results of evaluation of clinical samples of sputum from patients with or without active TB using CSIR 2.11 ssDNA aptamer in an ELONA readout platform. The cut-off for positive was set at an $OD_{450}$ above 0.2; denoted by the dotted line. The cut-off was determined by a 99% confidence interval of a known negative sample. CSIR 3.13 aptamer isolated from the same parental library against human CD7 was used as a negative control. Error bars denote standard deviations of experiments done in triplicate. Each sample was tested twice in two independent studies. The coefficient of variance between the two studies was less than 10% for all samples;

SELECTION OF APTAMERS

Figure 1:
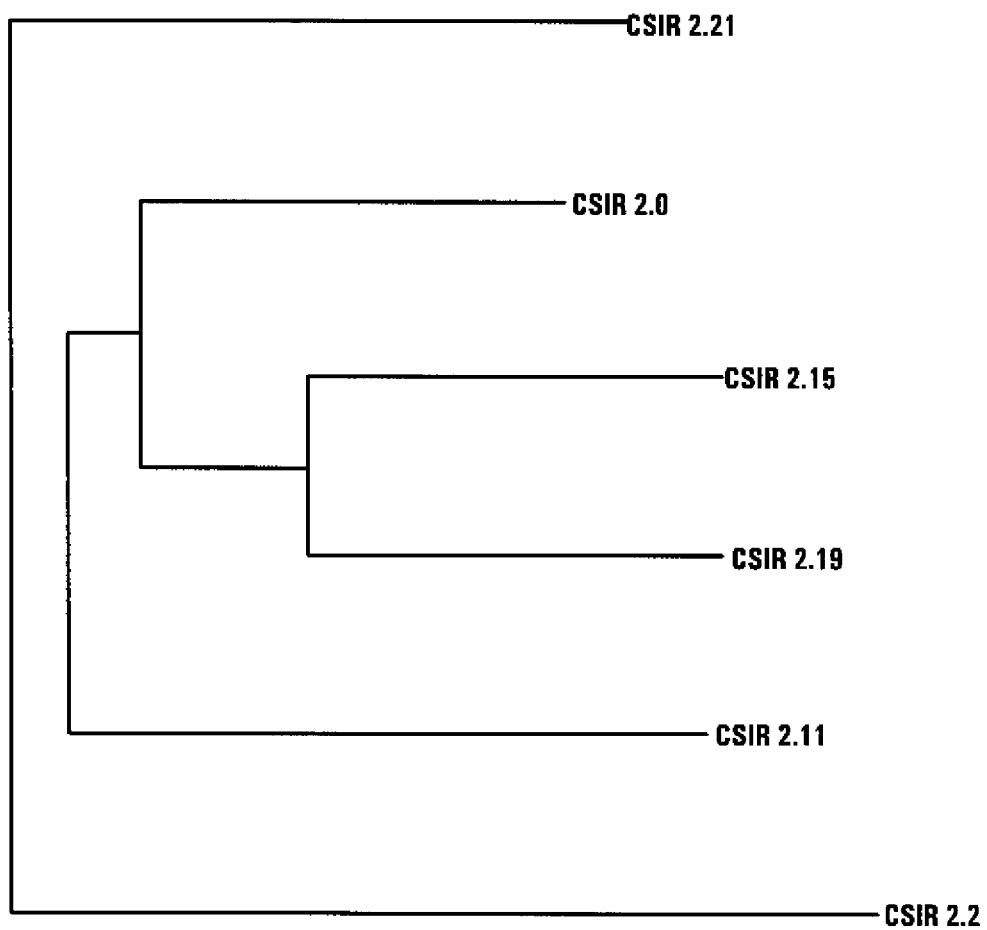

Selection of aptamers has been made possible by the development of a systematic evolution of ligands by exponential enrichment (SELEX) process. The SELEX process consists of several rounds of selection of sequences that bind to a target molecule. Each round consists of three main stages (1) incubating the oligonucleotide library with the target of interest, (2) separating bound targets from unbound targets using the desired partitioning method, and (3) amplifying the bound sequences.

Both single stranded DNA (ssDNA) and RNA libraries are used in different selections. These libraries typically consist of a random region of nucleotides that range from 20 to 60 nucleotides, although as few as 8 and as many as 220 random nucleotides can be used.

CFP-10.ESAT-6 Heterodimer

There are 23 ESAT-6-like genes in the Mtb H37Rv genome. These genes are located in 11 genomic loci and are named as EsxA-W. Inspection of the genetic diversity revealed that five out of eleven cases had the Esx genes are flanked by blocks of conserved genes. Besides the Esx genes, the other conserved regions encode proline-glutamic acid (PE) and proline-proline-glutamic acid (PPE) proteins, adenosine triphosphate (ATP) dependent chaperones of the ATPases associated with diverse cellular activities (AAA) family, membrane-bound ATPases, transmembrane proteins and serine proteases, which are known as mycosins. The 11 genomic regions are clustered in to five regions namely: region 1 spanning the genes rv3866-rv3883c; region 2 spanning genes rv3884c-rv3895c; region 3 spanning genes rv0282-rv0292; region 4 containing the genes rv3444crv3450c; and 5 containing the genes rv1782-rv1798. The genomes of Mtb H37Rv, *M. bovis* and *M. bovis* BCG have been compared, and various regions of difference (RD) have been identified. One of these regions, designated as RD1, is a 9500 bp region that is absent in all *M. bovis* BCG strains. This deletion entirely removes the genomic fragment from rv3872 to rv3879c. Among the lost genes are EsxB (rv3874) and EsxA (rv3875), which respectively encode CFP-10 and ESAT-6 proteins. This deletion is thought to be responsible for the primary attenuation of *M. bovis* to *M. bovis* BCG.

Function of the CFP-10 and ESAT-6

The two proteins are potent T-cell antigens recognised by over 70% of tuberculosis patients, which has led to their proposed use as a diagnostic reagent for tuberculosis in both humans and animals.

Functions of the Monomer and the Heterodimer

ESAT-6 alone or in combination with CFP-10 enhances the permeability of artificial membranes, by disrupting the lipid bilayers and acts as a cytolysin, while the exposed C-terminal region of CFP-10 may be involved in interactions with a host cell target protein resulting in stabilisation of the helical conformation.

Both proteins are important in both pathogenesis and virulence of M. tb as the CFP-10.ESAT-6 secretion system contributes to the arrest of phagosome maturation and promotes survival of mycobacteria within macrophages, which provides a novel link between the CFP-10.ESAT-6 secretion system and mycobacterial virulence and pathogenesis, however it is unclear as to whether it is ESAT-6, CFP-10 or the complex which is responsible for the arrest of phagosome maturation.

Biochemical Pathway of the Heterodimer

Both CFP-10 and ESAT-6 are secreted by the ESAT-6 system-1 (ESX-1), a dedicated secretion apparatus encoded by genes flanking EsxA and EsxB in the extended RD1 region. Among the proteins predicted to be involved in this process are a member of the AAA-family of ATPases (Rv3868), which may perform chaperone-like functions by assisting in the assembly and disassembly of protein complexes and several putative membrane proteins or ATP binding sites, which could be involved in forming a transmembrane channel for the translocation of the effector molecules.

Why the Heterodimer is Important

The expression characteristics of both proteins, together with their structural properties, have led RENSHAW, P. S., PANAGIOTIDOU, P., WHELAN, A., GORDON, S. V., HEWINSON, R. G., WILLIAMSON, R. A. & CARR, M. D., (2002), *Conclusive evidence that the major T-cell antigens of the Mycobacterium tuberculosis complex ESAT-6 and CFP-10 form a tight, 1:1 complex and characterization of the structural properties of ESAT-6, CFP-10, and the ESAT-6/CFP-10 complex. Implications for pathogenesis and virulence*, J Biol Chem, 277, 21598-603, to propose that the biologically active form is the heterodimer. This implies that ESAT-6, without its partner CFP-10, might not be active. The virulence of Mtb is reduced by the knockout of either ESAT-6 or CFP-10; therefore the heterodimer is very important in the virulence of M. tb. It has also been reported that the CFP-10.ESAT-6 complex acts as a signalling molecule, which is likely to lead to the heterodimer being a key player in diagnostics.

Characterisation of the CFP-10.ESAT-6 Heterodimer the Characteristics of the Heterodimer, Affinity of Binding, Location of the Heterodimer, Mechanism Overall, the surface features of the CFP-10.ESAT-6 complex seem most consistent with a function based on specific binding to one or more target proteins. The extensive contact surface between CFP-10 and ESAT-6 is essentially hydrophobic in nature and comprises about 25% of the total surface area of both proteins. The tight interaction between the two proteins in the complex appears to be primarily based on extensive and favourable van der Waals contacts, however, two salt bridges between CFP-10 and ESAT-6 appear to stabilize interactions between the N-terminal end of helix-1 in CFP-10 and the C-terminal end of the corresponding helix in ESAT-6, and between the C-terminal region of helix-2 in CFP-10 and the N-terminal region of the equivalent helix in ESAT-6, respectively.

EXAMPLE 1

Isolation of Aptamers Against CFP-10.ESAT-6 Heterodimer Aptamer Library

The first step in the SELEX experiments was to create a pool of variant sequences from which RNA or DNA aptamers of relatively high affinity for target proteins could be selected. For the DNA selection a 90-mer ssDNA randomized at 49 nucleotide positions flanked by primers were custom synthesized by Integrated DNA Technologies (CA, USA). The primers were: 5'-GCCTGTTGTGAGCCTCCTAAC-3' (forward primer) and 5'-GGGAGACAAGAATAAGCATG-3' (reverse primer modified with either T7 promoter region (TAATACGACTCACTATA) or a phosphate at the 3' end). The library used was 5'-GCCTGTTGTGAGCCTCCTAAC (N49) CATGCTTATTCTTGTCTCCC-3'.

In Vitro Selection of DNA Aptamers

In the first round of selection 500 pmol of ssDNA library was used to obtain a diversity of at least $10^{14}$ molecules of random sequence. The selection was done by a modification of the SELEX protocol in which the ssDNA-protein complexes are partitioned and purified using a nitrocellulose membrane. Before selection, the ssDNA library was incubated with a nitrocellulose membrane to eliminate any membrane binders.

The ssDNA library was refolded at 95° C. for 10 minutes, immediately cooled on ice for 5 minutes and then left to reach room temperature in the HMCKN binding buffer (20 mM Hepes (Sigma), 2 mM $MgCl_2$ (Sigma), 2 mM $CaCl_2$ (Sigma), 2 mM KCl (Sigma) and 150 mM NaCl (Sigma), pH 7.4). This was then either incubated with 1590 nM of CFP-10.ESAT-6 heterodimer for 1 hour at 37° C. or immediately used in a no protein control which was directly filtered on the nitrocellulose membrane. The ssDNA-protein complex was passed through a nitrocellulose membrane. Non-specifically bound ssDNA was removed with two washes of HMCKN binding buffer. Bound ssDNA was eluted by cutting the membrane and placing the pieces in a elution buffer (7M urea (Sigma), 100 mM sodium citrate (Sigma) and 3 mM EDTA (Sigma)) and heated to 100° C. for 5 minutes. Then phenol/chloroform was added and left to incubate for a further 25 minutes before extraction. This was followed by chloroform extraction and an ethanol precipitation.

Recovered ssDNA was amplified using polymerase chain reaction (PCR) under mutagenic conditions to increase the diversity of the molecules. This dsDNA was then used in three different methods to generate ssDNA, the three methods were then used as three independent selection methods. The first method was to incorporate a biotin label during PCR using a biotin labelled reverse primer. The dsDNA was then added to streptavidin magnetic beads (Invitrogen) and the two strands were separated using 0.3 M HCl solution or 95° C. for 5 minutes. The resulting ssDNA was cleaned and used as a template for the next round of selection (this method is referred to as 'biotin-based selection'). The second method used the dsDNA as a template for in vitro transcription to obtain RNA. The RNA was DNAse treated, cleaned and precipitated and used as the template for RT PCR to obtain cDNA. The cDNA-RNA complex was treated with a 1 M NaOH (Sigma), 0.5 M EDTA (Sigma) buffer to hydrolyse the RNA. The resulting cDNA was used as a template for the next round of selection (this method is referred to as 'T7-based selection'). The third method used to obtain ssDNA by including a phosphate labelled reverse primer in the PCR. The dsDNA was then cleaned up and treated with lambda exonuclease (New England Biolabs, Anatech), this results in the degradation of the reverse strand with the phosphate modification. The resulting ssDNA was then cleaned up and used as a template for the next round of selection (this method is referred to as 'exonuclease-based selection').

Selection of aptamers against the CFP-10.ESAT-6 heterodimer was done using a modified SELEX protocol. Different approaches for partitioning were used.

A single stranded DNA library was used for the selection of aptamers. After each round of selection using the nitrocellulose membrane for partitioning, a dsDNA PCR was done to optimise the number of cycles needed to convert ssDNA to dsDNA and amplify the selected pool.

Based on the optimisation of the dsDNA PCR the number of cycles giving a single band at 90 bp was used to produce dsDNA. The optimised number of cycles was 12 in both selections. The dsDNA was then used to generate the ssDNA using one of the three methods (biotin, T7- and exonuclease-based selections). The ssDNA obtained from each round was run on a native PAGE gel to ensure that the ssDNA obtained was clean for use in the next round of selection.

The biotin-based selection failed as the two strands could not be separated and the dsDNA remained bound to the beads. Due to this, the biotin-based selection was abandoned after the first round of selection. The T7-based selection resulted in an enrichment of 54.7% after 6 rounds of selection and the exonuclease-based selection had an enrichment of 68% after 4 rounds of selection. The two pools from the two selections were then cloned and sequenced, respectively.

EXAMPLE 2

Cloning and Sequencing of ssDNA Aptamers

The aptamer pool from the $5^{th}$ (T7-based selection) and $3^{rd}$ (exonuclease-based selection) SELEX round were subjected to a negative selection against the nitrocellulose membrane alone. The pools recovered after negative selections were put through a final ($6^{th}$—T7-based selection and 4th—exonuclease-based selection) SELEX round. In this last round, both pools of ssDNA were amplified subsequently with the phosphate modified reverse primer and ligated into the pGEM-T easy vector (Promega, Whitehead Scientific). *E. coli* TOP10 cells (Novagen, Merck) were transformed using these vector constructs. After transformation 244 colonies were picked and spread onto duplicate LB agar (Sigma) plates containing 100 μg/ml of ampicillin (Fermentas, Inqaba Biotech) and IPTG (Fermentas, Inqaba Biotech) for blue white colony screening. One plate was used for colony PCR screening using M13 primers (IDT, Whitehead Scientific) and to prepare overnight cultures for glycerol stocks. The other plate was sent to Inqaba Biotech for sequencing with the universal M13 primers (Inqaba Biotech). Sequence analysis and alignments were performed using Bioedit. The analysis of secondary structure of aptamers was performed by free energy minimisation algorithm according to Zuker using mfold (www.bioinfo.rpi.edu/applications/mfold/).

Of the 244 colonies on the duplicate plates a few were selected for colony PCR screening using the universal M13 primers to determine if they had the insert or not. The T7 selection clones seemed to all have the insert whereas the exonuclease clones picked for screening were insert negative. All clones on the plates were sequenced.

All 244 clones were sent for sequencing and the sequences were analysed using BioEdit. From the 244 sequences, 104 were insert positive (11 from the exonuclease selection and 93 from the T7 selection), this confirmed the results seen in the PCR screen where most of the exonuclease clones were insert negative. Of the 104 sequences that were analysed, 66 were unique and 15 sequences had two or more repeats, 6 aptamers showed significant binding (FIG. 1 and Table 1).

TABLE 1

Sequences (5'-3' direction) of ssDNA aptamers that significantly bound the CFP-10.ESAT-6 M. tb target antigen

```
                   10        20        30        40        50        60        70        80        90
CSIR 2.2  GCCTGTTGTGAGCCTCCTAAC~CCGTCTAACGAGATTGGGTCTTCATATGGCTCGAAGCGCGCGGTCAGTT~CATGCTTATTCTTGTCTCCC
CSIR 2.9  GCCTGTTGTGAGCCTCCTAAC~TCCGGTCTTCAACATGTCCAATCGAACTTCGGCGGAAATCCTTTACCTG~CATGCTTATTCTTGTCTCCC
CSIR 2.11 GCCTGTTGTGAGCCTCCTAAC~CCCATCTTATACGTATATGGACTCATCTCGACCCCCGATAGGCTTGGTA~CATGCTTATTCTTGTCTCCC
CSIR 2.15 GCCTGTTGTGAGCCTCCTAAC~TAATGTGGATGCTGCATCGTTAGTATTTCTAGCATGCAATATAGGCATG~CATGCTTATTCTTGTCTCCC
CSIR 2.19 GCCTGTTGTGAGCCTCCTAAC~TTCCAATAACGATACTTAAACCTGGTCTTTGCCAGTCAATGATAGCAT~~CATGCTTATTCTTGTCTCCC
CSIR 2.21 GCCTGTTGTGAGCCTCCTAAC~ACACACGTAGCGCCTTGTTGAAGTATACTCAAAGCATTCTCCACGCGGG~CATGCTTATTCTTGTCTCCC
```

EXAMPLE 3

Binding Assay of ssDNA Aptamers by ELONA

The assay was modified from an ELISA protocols for determination of aptamer-protein interactions and has been termed an ELONA. Unique aptamer clones identified by sequencing were tested for their individual binding characteristic to the CFP-10.ESAT-6 heterodimer using an ELONA. Each ssDNA aptamer was prepared using the exonuclease method as described above with minor modifications, in that all aptamers were prepared with the biotinylated forward primer. For each binding assay, 96 well micro-titre plates (Corning, Adcock Ingram) were coated with the CFP-10.ESAT-6 heterodimer in a 10 mM $NaHCO_3$ buffer pH 8.5 (Sigma) and left overnight at 4° C. The plates were then washed with 1× phosphate buffered saline containing 0.005% Tween 20 (PBS-T) pH7 (Sigma) and blocked with a 5% fat free milk solution for 1 hour at 4° C. The plates were then washed 3 times with a 1×PBS after which 150 nM biotinylated aptamer was added and incubated for 2 hours at room temperature. This was followed by three wash steps with 1×PBS-T and the addition to HRP-conjugated streptavidin (diluted 1:10000 in 1×PBS-T) and incubated for two hours at 37° C. The plates were then washed four more times with 1×PBS-T, after which a final 3,3',5,5'-tetramethylbenzidine (TMB) detection substrate (Separations) was added. A change in colour to blue, which could be observed with a naked eye, indicated that the aptamers bound to the CFP-10.ESAT-6 heterodimer. The reaction was stopped with a 2 M sulphuric acid solution (Merck), resulting in a colour change from blue to yellow. The plates were read on the MultiSkan Go plate reader (ThermoScientific, AEC-Amersham) at a wavelength of 450 nm. Each plate had a CFP-10.ESAT-6 and an aptamer alone control, which were averaged and then subtracted from each well to eliminate background noise. Each aptamer was done in triplicate and the repeats were averaged and the standard deviation calculated. Each aptamer was tested twice in triplicate to ensure accuracy. The aptamers were then compared to the aptamer alone control using a Student t-test statistical analysis to obtain the p value for significance.

Figure 2:
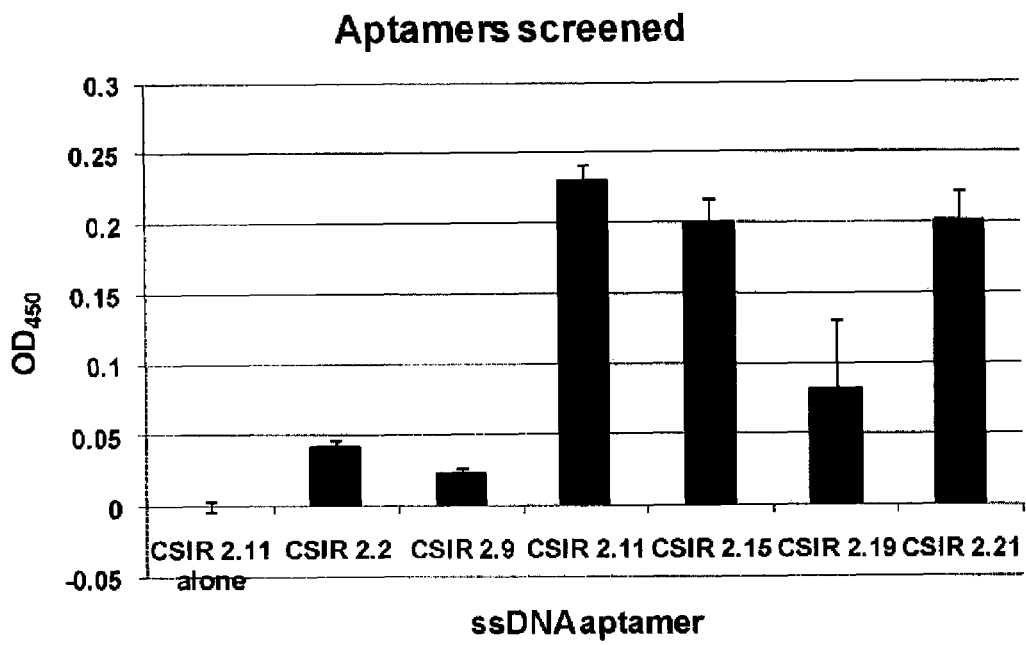

The binding ability of individual aptamers was tested using an ELONA. Out of the 66 biotinylated ssDNA aptamers screened by ELONA against the CFP-10.ESAT-6 heterodimer, 24 bound significantly (p<0.05) (FIG. 2).

EXAMPLE 4

Determination of Antibody Competition Binding of Individual ssDNA Aptamers by ELONA Only the 24 aptamers that bound significantly to the heterodimer were used in further studies. The antibody competition binding was done using the ELONA method described above with minor modifications. The antibody was bound to the plate; then blocked followed by the addition of the heterodimer. The biotinylated aptamer was the added, followed by the HRP-conjugated streptavidin. Each combination was done in triplicate and repeated in two independent assays. The antibody competition data was compared with the binding assay to identify differences in binding capacity of the aptamers in the presence of the antibody. Although the competition assay and binding assay were done on different plates, the positive control (protein and aptamer CSIR 2.11) were run on both plates with similar results to normalise the data on the two plates.

Figure 3:
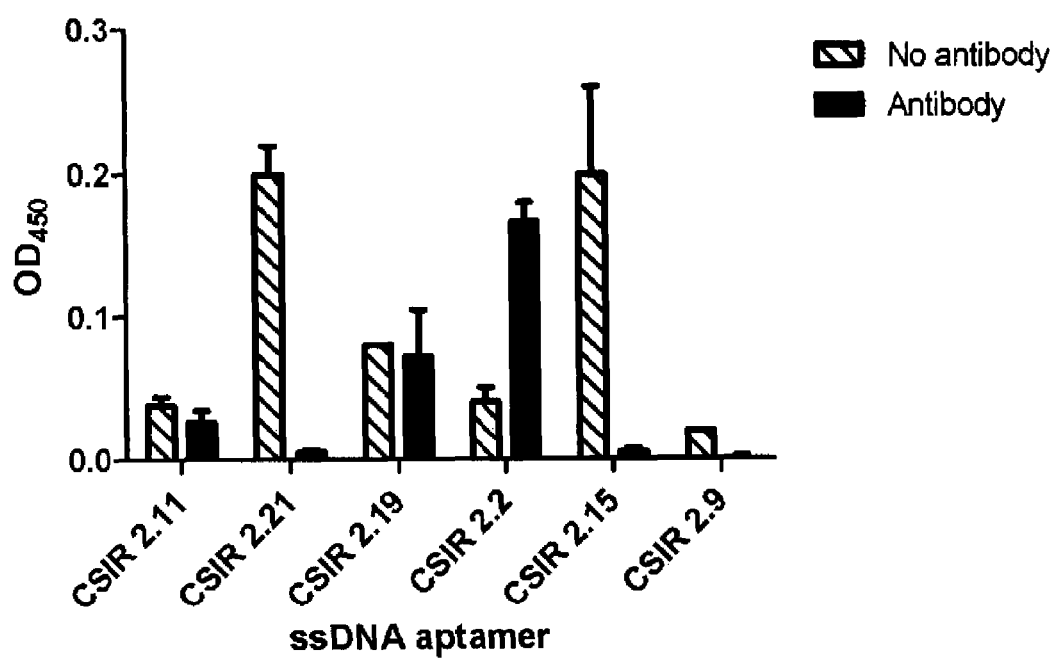

The positive control ran on both plates was used to normalise the results between ELONA experiments. Binding of some ssDNA aptamers such as CSIR 2.15, CSIR 2.9 and CSIR 2.21 was abrogated by the presence of anti-ESAT-6 monoclonal antibody while binding of other aptamers such as CSIR 2.2 and CSIR 2.12 was enhanced by the presence of the anti-ESAT-6 monoclonal antibody (FIG. 3). Taken together, these data suggest that some aptamers such as CSIR 2.15, CSIR 2.9 and CSIR 2.21 bind to a similar epitope on the heterodimer as that recognised by the anti-ESAT-6 monoclonal antibody while others such as CSIR 2.2 and CSIR 2.12 bind to more distant and unique epitopes.

EXAMPLE 5

Determination of Monomer Binding and Specificity of Individual Aptamers by ELONA Selected ssDNA aptamers were tested for binding specificity to the ESAT-6 and CFP-10 monomers. The aptamers were tested for binding using ELONA to CFP-10, ESAT-6, CFP-10.ESAT-6 heterodimer, a CFP-10.ESAT-6 related protein in the ESX3 secretion system (EsxGH complex) and a HIV surface glycoprotein (gp120). EsxGH is an ESAT-6 family related protein that is encoded and secreted by the ESX-3 secretion system and gp120 is a HIV glycoprotein which is unrelated to the Mtb antigens.

CSIR 2.11 aptamer was used to test the specificity of the aptamer in relation to other bacterial lysates. Lysates were obtained by bead beating 100 ml of cultures of *Pseudomonas aeruginosa* (Pseudomonas), *Streptococcus pyogenes* (Streptococcus), *Mycobacterium smegmatis* (Smegmatis) and the auxotroph of *Mycobacterium tuberculosis* (Auxotroph). The cutoff for specificity was determined by a 99% confidence interval of a known negative sample.

Figure 4:
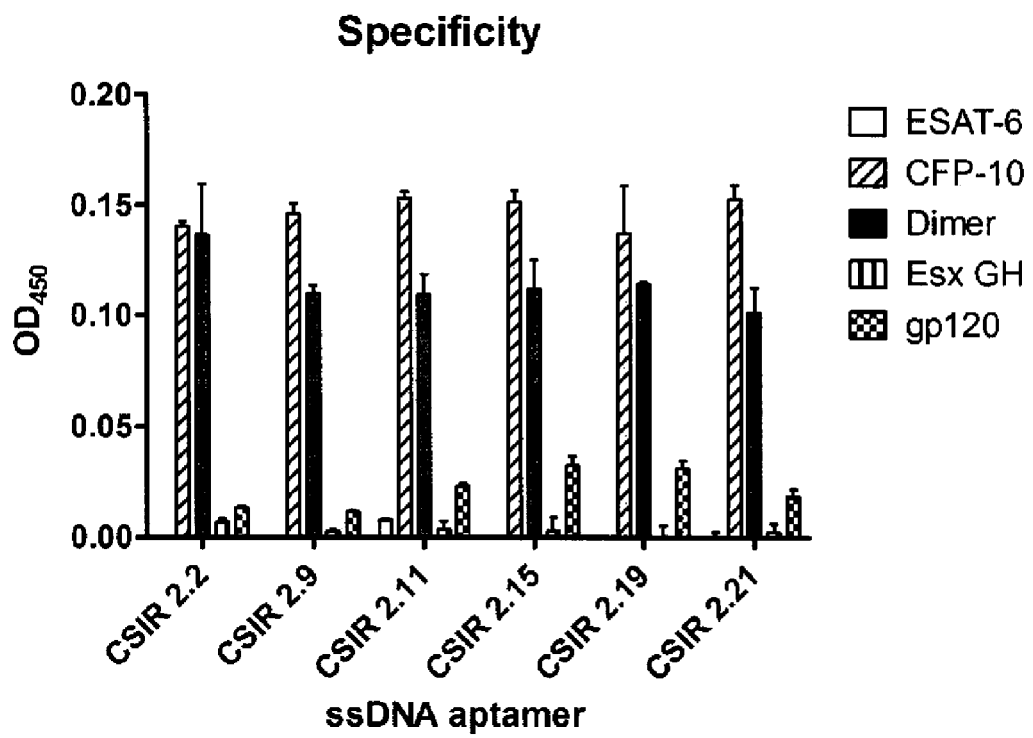

The 24 ssDNA aptamers that significantly bind to the heterodimer were tested for monomer binding and specificity. The proteins used for specificity screening were the monomers (CFP-10 and ESAT-6), the heterodimer (CFP-10.ESAT-6), an ESAT-6 family heterodimer (EsxGH) and an unrelated protein (gp120). While most aptamers specifically bound the CFP-10.ESAT-6 heterodimer, interestingly, two of the 24 aptamers (CSIR 2.1 and CSIR 2.12) also bound gp120 to a similar extent or better than the CFP-10.ESAT-6 heterodimer (FIG. 4). None of the aptamers were able to detect EsxGH (FIG. 4). It was also interesting to note that while most aptamers also recognised the CFP-10 monomer in addition to the CFP-10.ESAT-6 heterodimer; none of the 24 aptamers screened recognised the ESAT-6 monomer (FIG. 4).

Figure 5:
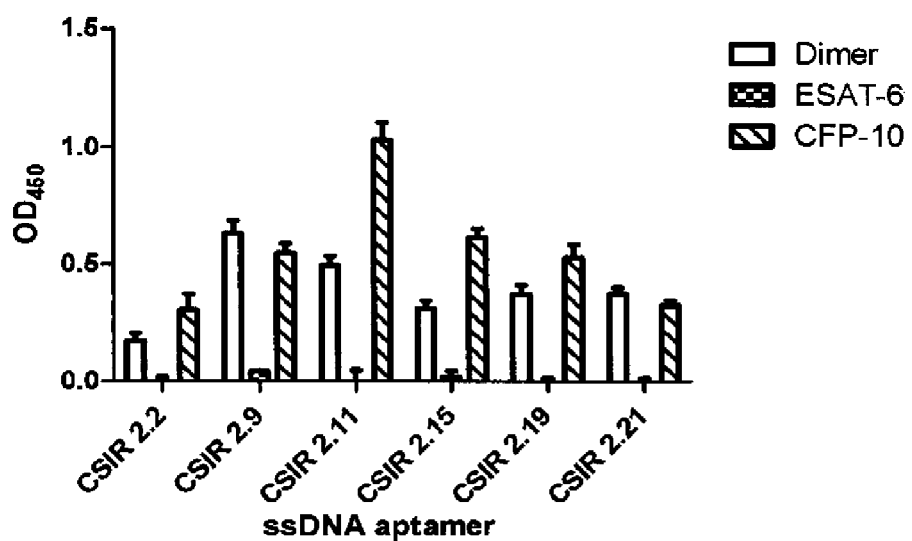
Figure 6:
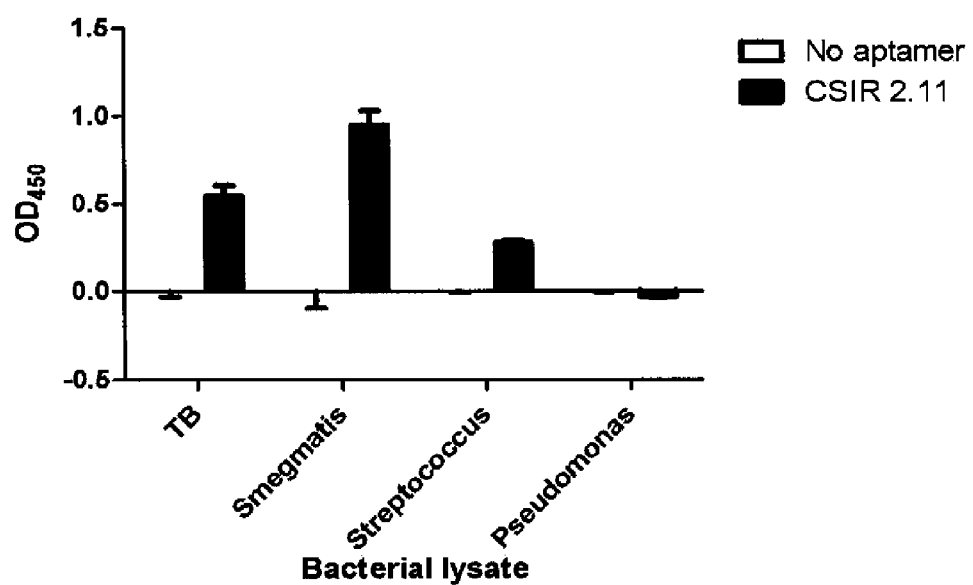
Figure 7:
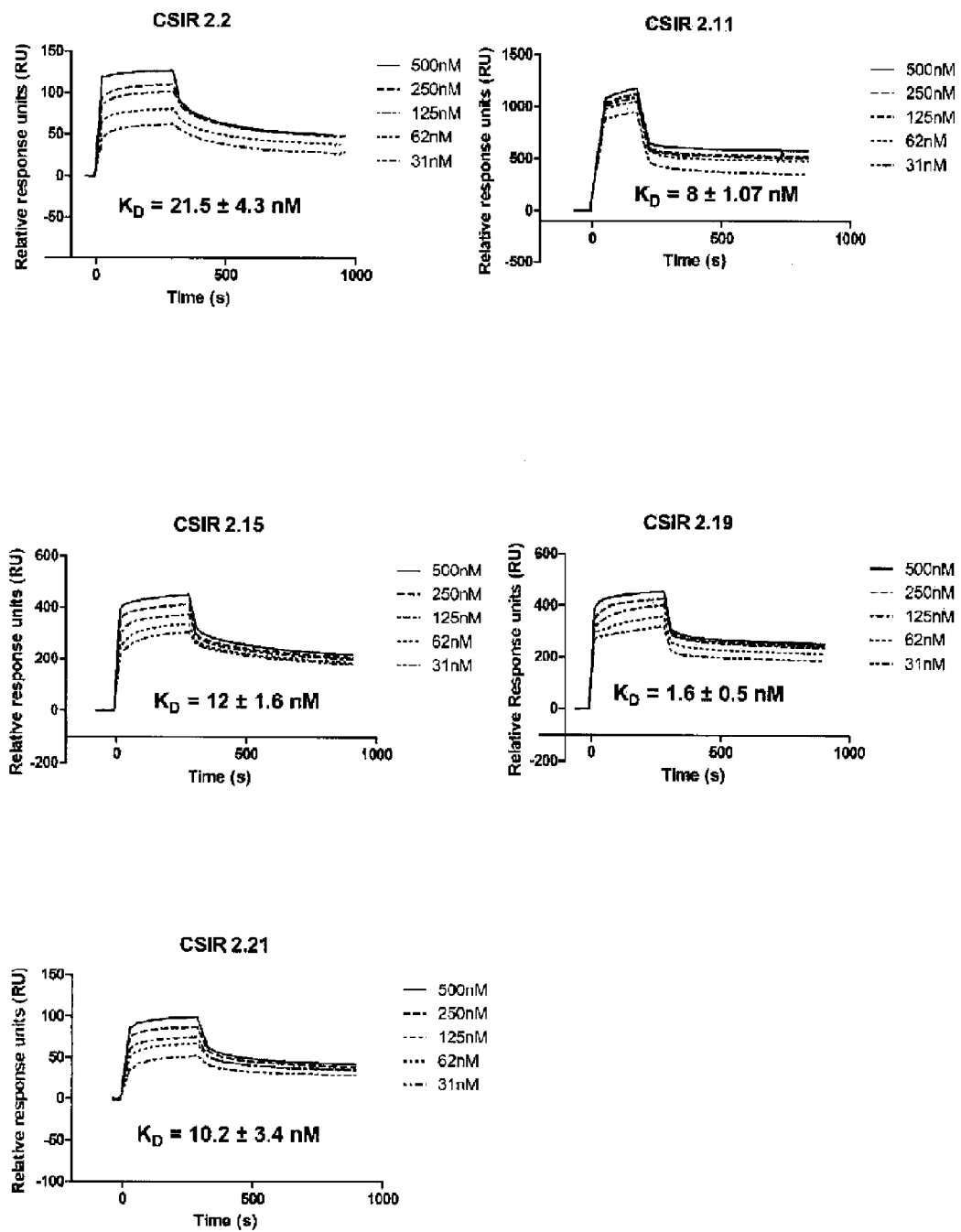
Figure 8:
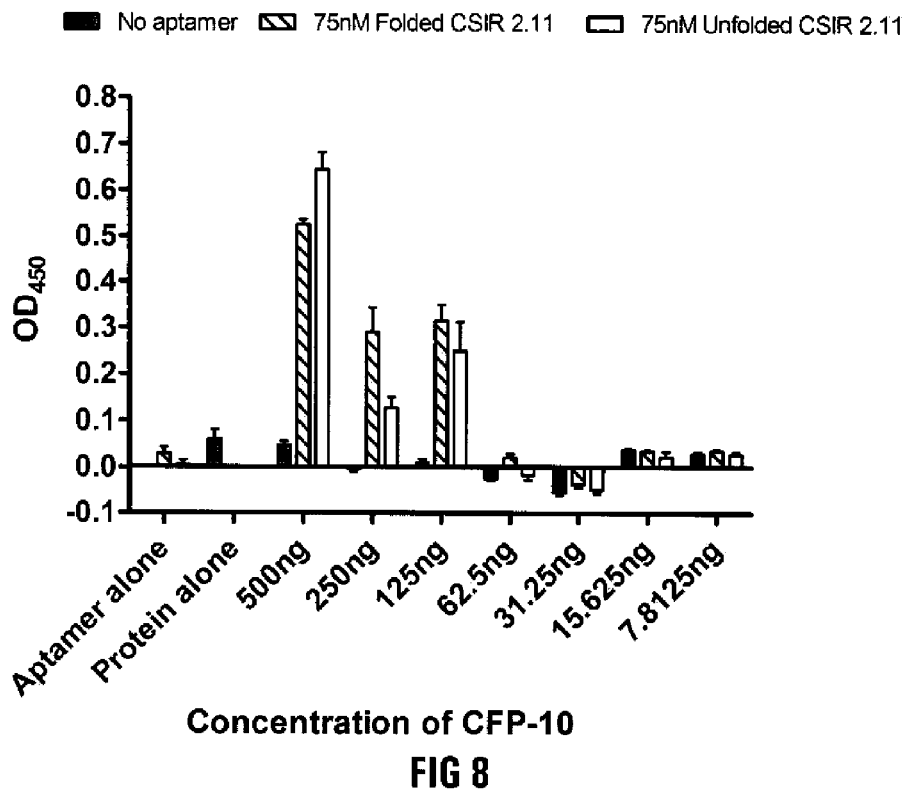
Figure 9:
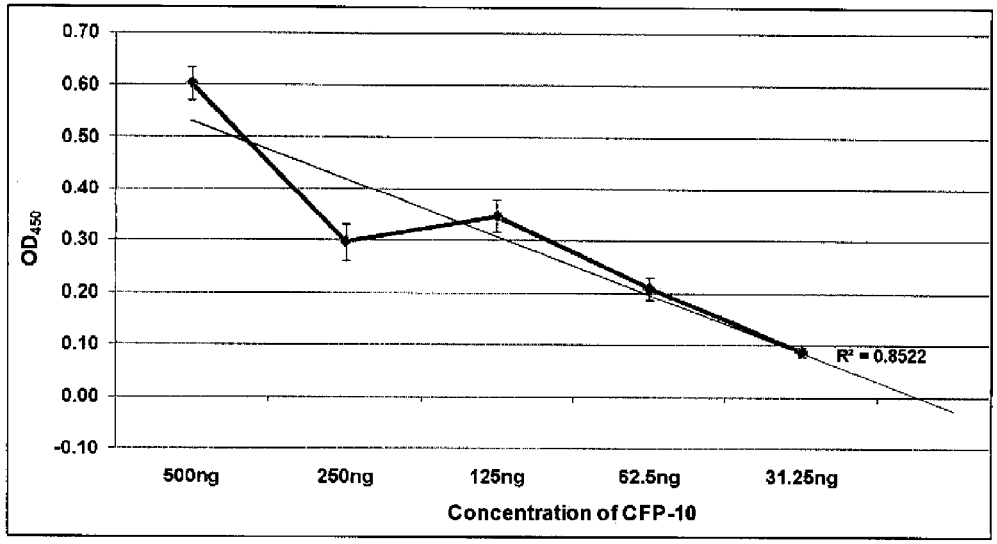

Six of the best aptamers were chosen and custom synthesized by Independent DNA Technologies (IDT) using the solid phase chemical manufacturing process. The six aptamers chosen were CSIR 2.2, CSIR 2.9, CSIR 2.15, CSIR 2.19, CSIR 2.21 and CSIR 2.11. The binding of these aptamers to their CFP-10.ESAT-6 M. tb target proteins, as well as to the CFP-10 and ESAT-6 monomers was repeated to confirm that the aptamers could be chemically synthesized at an industrial scale with a biotin modification and still retain their respective activities. Although the readings of all the synthesized aptamers gave higher readings (FIG. 5) when compared to the in vitro produced aptamers (FIG. 4), there was no significant difference between the aptamers synthesized in house by PCR and those custom synthesized by Independent DNA Technologies (IDT) using the solid phase process. The results were consistent because all the six aptamers also recognized the CFP-10.ESAT-6 heterodimer and the CFP-10 monomer but not the ESAT-6 monomer (FIG. 5).

CSIR 2.11 was chosen as one of the best aptamers for further specificity test against other bacterial lysate using the auxotroph strain of *Mycobacterium tuberculosis* (M. tb) as a positive control. CSIR 2.11 did not recognise pseudomonas or *streptococcus*, but recognised the lysate of *Mycobacteria smegmatis* (FIG. 6). This is not surprising as *Mycobacteria smegmatis* also secretes the CFP-10 protein.

EXAMPLE 6

Determination of the Dissociation Constant ($K_D$) of an Individual ssDNA Aptamer Using the BIAcore 3000

To determine the binding affinity of aptamers to the M.tb antigens, all four flow cells on a CM5 chip (BIAcore, Separations Scientific) were activated with EDC:NHS (BIAcore, Separations Scientific). CFP-10 was bound to three of the four flow cells by injecting 50 μl of 50 μg/ml CFP-10 over them. Ethanolamine (BIAcore, Separations Scientific) was then injected over all four flow cells to quench any remaining active sites. Partially bound or unbound protein was removed by a wash with 10 μl of a 10 mM NaOH solution. Different concentrations of the respective aptamers (0 nM, 31 nM, 62 nM, 125 nM, 250 nM, and 500 nM) were randomly injected over all four flow cells at a flow rate of 10 μl/min for 5 minutes. The respective aptamers, were then allowed to dissociate for 10 minutes. The flow cell that did not have the aptamer was used as the blank flow cell to subtract non-specific binding. The evaluation was done using BiaEvaluation Software (BIAcore) to determine the $K_D$ values for each flow cell. The average dissociation constant was then determined.

The dissociation constant ($K_D$) of 5 selected aptamers, CSIR 2.2; CSIR 2.11; CSIR 2.15; CSIR 2.19 and CSIR 2.19 were determined using the BIAcore surface plasmon resonance technology. CSIR 2.19 had the lowest $K_D$ at 1.6±0.5 nM, while CSIR 2.11 had a $K_D$ of 8±1.07 nM and CSIR 2.2 had comparatively the highest $K_D$ at 21.5±4.3 nM (FIG. 7).

EXAMPLE 7

Determination of Whether Aptamer Folding Affects the Binding to the Target

It was important to determine if the aptamers needed to be refolded for further studies as this would impact on their downstream application. One batch of CSIR 2.11 aptamer was folded as described above while another batch was used directly after thawing to determine if the aptamer could be used without the refolding step. An ELONA was preformed with both batches of aptamer against CFP-10. The results show that the aptamer can be used directly from the freezer without the refolding step (FIG. 8).

EXAMPLE 8

Limit of Detection

CFP-10 was bound to a 96 well plate (Corning, Adcock Ingram) in serial dilutions in a $NaHCO_3$ buffer and left overnight at 4° C. The plates were then washed with 1× phosphate buffer saline solution containing 0.005% Tween 20 (PBS-T) pH7 (Sigma) and blocked with a 5% fat free milk solution for 1 hour at 4° C. The plates were then washed 3 times with a 1×PBS-T after which 150 nM biotinylated EA10 aptamer was added and incubated for 2 hours at room temperature. This was followed by three wash steps with 1×PBS-T and the addition of HRP-conjugated streptavidin (diluted 1:10000 in 1×PBS-T) and incubated for two hours at 37° C. The plates were then washed four more times with 1×PBS-T, after which the 3,3',5,5'-tetramethylbenzidine (TMB) detection substrate (Separations) was added. A change in colour to blue, which could be observed with a naked eye, indicated that the aptamers bound to the CFP-10 protein. The reaction was stop with a 2 M sulphuric acid solution (Merck), at which point the blue colour observed changes to yellow. The plates were then read on the MultiSkan Go plate reader (ThermoScientific, AEC-Amersham) at a wavelength of 450 nm. Each plate had a CFP-10 and an aptamer alone control, which were averaged and then subtracted from each well to eliminate background noise. Each dilution was done in triplicate, the repeats averaged and the standard deviation calculated.

Serial dilutions of CFP-10 coated on a 96 well micro-titer plate showed that 150 nM of CSIR 2.11 aptamer is able to detect as little as 31 ng of CFP-10 (FIG. 9). The best fit curve had an $R^2$ value of 0.85.

EXAMPLE 9

Evaluation of Clinical Samples from Patients with or without Active TB

Twenty sputum samples that had been well characterized (Table 2) were used. Briefly, they included: (a) smear positive—culture positive; (b) smear negative—culture positive; (c) smear negative—culture negative, quantiferon positive and TSPOT positive; and (d) smear negative—culture negative, quantiferon negative and TSPOT negative. These sputum samples had been liquefied in a 0.1% dithiothreitol (DTT) solution. The sputum samples were bound to a 96 well micro-titer plate (Corning, Adcock Ingram) in a $NaHCO_3$ buffer and left overnight at 4° C. The plates were then washed with 1×PBS-T pH7 and blocked with a 5% fat free milk solution for 1 hour at 4° C. The plates were then washed 3 times with a 1×PBS-T after which 300 nM biotinylated EA10 aptamer was added and incubated for 2 hours at room temperature. This was followed by three wash steps with 1×PBS-T and the addition of HRP-conjugated streptavidin (diluted 1:10000 in 1×PBS-T) and incubated for two hours at 37° C. The plates were washed four more times with 1×PBS-T, after which a final TMB (Separations) detection substrate was added. A change in colour to blue, which could be observed with a naked eye, indicated that the aptamers bound to the CFP-10 protein. The reaction was stopped with a 2 M sulphuric acid solution (Merck) at which point the blue colour observed changed to yellow. The plates were then read on the MultiSkan Go plate reader (ThermoScientific, AEC-Amersham) at a wavelength of 450 nm. Each plate had an aptamer alone control, which were averaged and then subtracted from each well to eliminate background noise. Each sample was done in triplicate, averaged and the standard deviation was calculated; the experiment was repeated twice to determine repeatability of the assay. An aptamer selected from the same library against a different target was used as a control (CSIR 3.13). The cutoff for specificity was determined by a 99% confidence interval of a known negative sample.

TABLE 2

Characteristics of sputum samples obtained from patients with or without active TB. Based on the results of tests used to characterise the samples, the samples were broadly classified as No TB; Latent TB; or Active TB as denoted in the parenthesis. Numbers were assigned to the samples during the study in order to match the patients' numbers.

| Smear negative - culture negative, quantiferon negative and TSPOT negative (No TB) | Smear negative - culture negative, quantiferon positive and TSPOT positive (Latent TB) | Smear negative - culture positive (Active TB) | Smear positive - culture positive (Active TB) |
|---|---|---|---|
| 35 | 54 | 11 | 5 |
| 52 | 66 | 36 | 17 |
| 139 | 67 | 65 | 39 |
| 143 | 76 | 85 | 59 |
| 161 | 101 | 88 | 94 |

Figure 10:
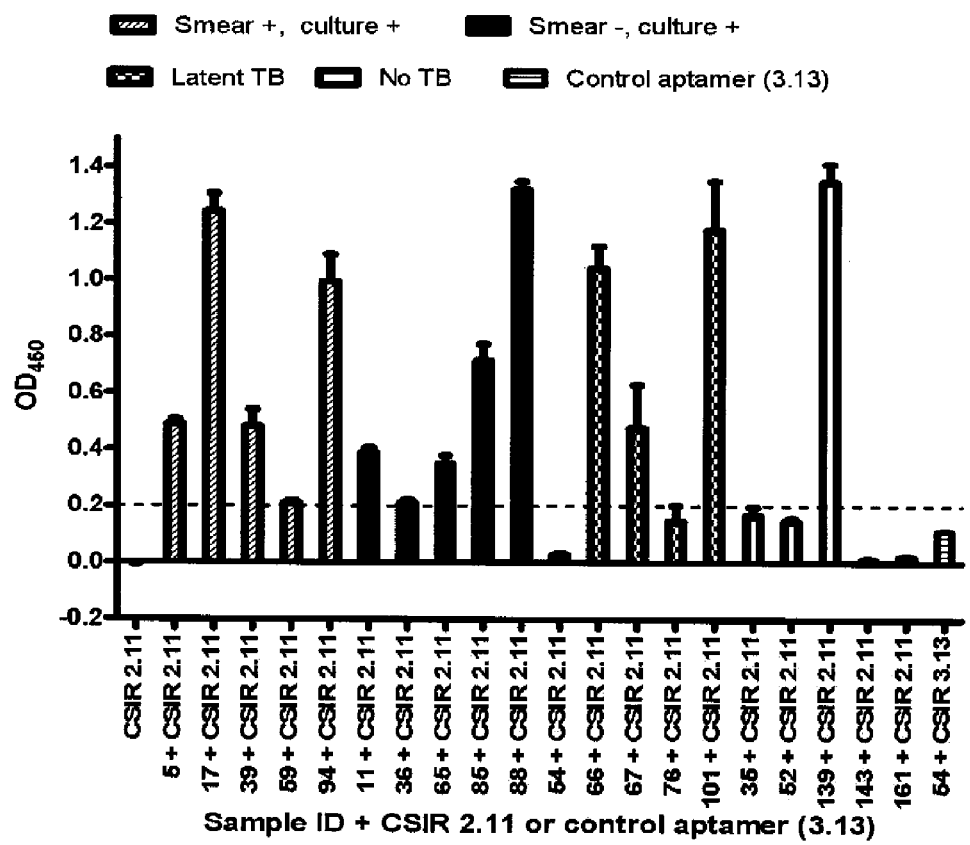
Figure 14:
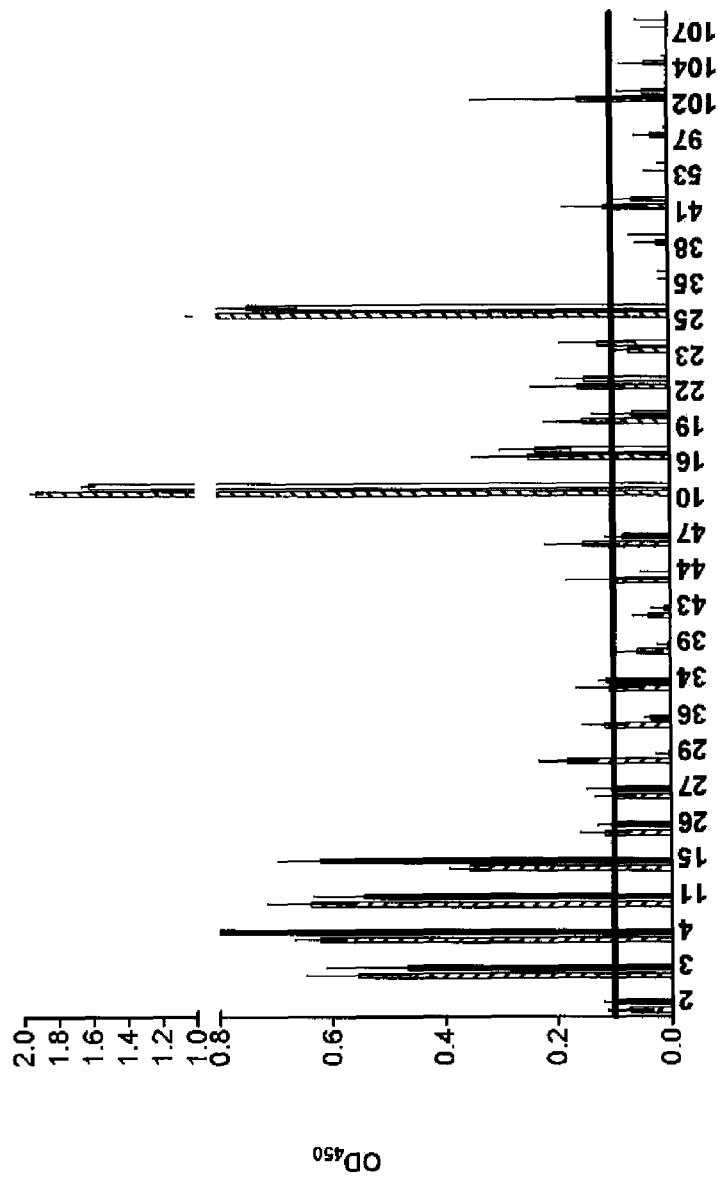
FIG. 14 shows, for Example 12, a comparison of CSIR 2.11 and CSIR 2.21 using sputum samples.

The CSIR 2.11 ssDNA aptamer was able to accurately detect 4 of the 5 smear positive—culture positive samples as positive (80%), 4 of the 5 smear negative—culture positive samples as positive (80%); but it also detected one sample classified as no TB (sample 139, which is all negative for quantiferon, TSPOT, smear and culture tests), as positive (FIG. 10). In addition, CSIR 2.11 detected 3 of the 5 samples classified as latent TB (quantiferon and TSPOT positive but smear and culture negative) as positive (FIG. 14). The control ssDNA aptamer, CSIR 3.13, which was derived from the same parental library but isolated against, and specific for human CD7 was negative for all the samples, as expected (data shown for only 1 sample on FIG. 10). The cut-off for negative results using the aptamers was determined to be an $OD_{450}$ below 0.2 at 99% confidence interval based on a known negative sample (FIG. 10). Taken together, and based on the classification for latent TB used in characterizing the samples, CSIR 2.11 ssDNA aptamer had a specificity of 60% (i.e. correctly identified 6/10 samples as negative) and a sensitivity of 80% (i.e. correctly identified 8/10 samples as positive) using the ELONA readout platform. Notwithstanding, two of the false negatives samples in this study (samples 36 and 59) were inconclusive because they were on the border line of the cut-off (FIG. 10). If they were taken as positive the sensitivity of CSIR 2.11 would increase from 80% to 100%.

Figure 11:
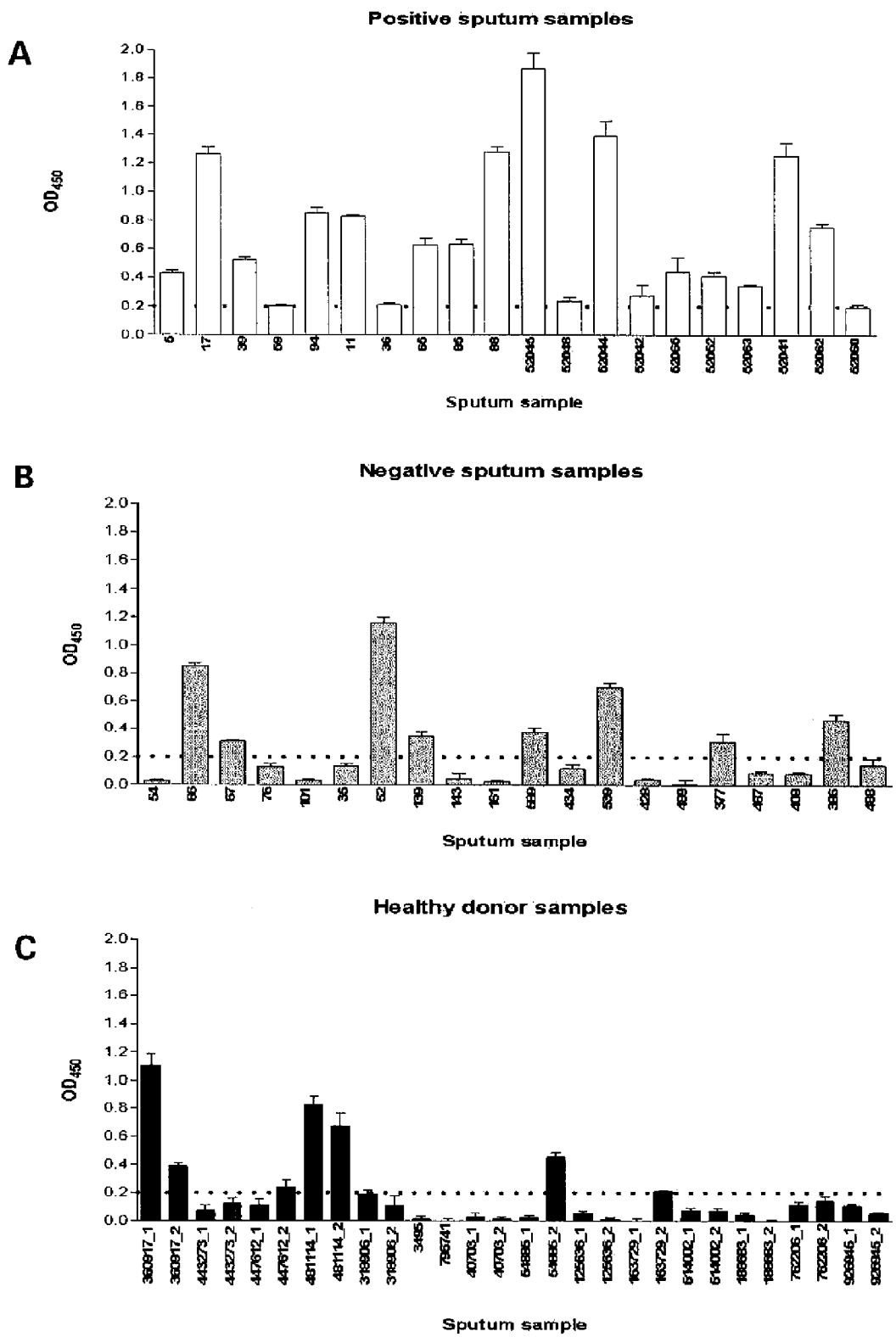
FIG. 11 shows, for Example 9, an evaluation of sputum samples using CSIR 2.11 as a detection reagent.

Evaluation of 80 sputum samples using CSIR 2.11 as detection reagent was conducted, the results of which are illustrated in FIG. 11. The aptamer was tested on three groups of samples (A) Definite TB, (B) Latent TB and TB negative and (C) healthy laboratory volunteers. Using Youden's index, the cut-point for positive samples was set at an OD450 of 0.2 and is indicated by the dotted line. Data are presented as mean±standard deviation of the mean.

Current diagnostics for TB have many disadvantages, especially when used in resource-poor settings, which also happen to be high in TB incidence and prevalence. The current gold standard for TB diagnostics is a combination of smear microscopy and culture methods. The advantage of smear microscopy is the relatively low cost. The main disadvantage is that smear microscopy has low sensitivity (35-75%), especially among HIV positive patients. While the culture method increases sensitivity to over 90%, it takes 6-8 weeks to get results and the method also requires highly trained personnel and specialized containment level 3 facilities. The culture method currently costs about $10 per sample, excluding the exorbitant costs of establishing and maintaining a containment level 3 laboratory. There seem to be a correlation between the duration of test, cost of test and sensitivity. Serological tests are rapid and relatively inexpensive but have poor sensitivity (16-75%), NAATs are rapid but only have a sensitivity of 60-70%. The GeneXpert® is a fully automated molecular test with a sensitivity of 60-80% but is currently not a cost effective method for poor resource settings. It currently costs about $20 USD per sample, excluding the high price of the instrument. Despite current achievements, there is still a need for an Affordable, Sensitive, Specific, User-friendly, Rapid, Equipment-free and Deliverable to end user (ASSURED) TB diagnostics.

DNA aptamers by virtue of their simplicity, specificity, sensitivity and low costs of production can serve as ASSURED TB diagnostics, thus meeting the needs of a diagnostic tool that is required in underdeveloped and high burden TB countries. In a current proof-of-concept study, using the ELONA readout platform, we showed that a single stranded DNA aptamer called CSIR 2.11 isolated against the CFP-10.ESAT-6 Mycobacterium tuberculosis target protein can detect TB in well characterized clinical sputum samples of TB patients from a high HIV prevalence country with a sensitivity of 80-100% and specificity of 60% if latent TB is considered negative.

The two false negative readings are on the border line of the cut-off and the results are thus inconclusive. They could be classed as either positive or negative. The reason for the strikingly false positive sample (139) is hard to find, unless the sample was cross-contaminated during the process of acquiring sputum and/or during sample preparation and storage.

The low cost of $0.52 USD (R3.67 ZAR) per sample for the aptamer-based ELONA for TB detection and the rest of data in general, including the 80-100% sensitivity, demonstrate that the aptamers of the present invention can be used successfully and economically in ASSURED TB diagnostics.

EXAMPLE 10

Further characterisation and optimisation of the anti-ESAT-6.CFP-10 aptamers yielded active, affordable TB detection molecules for the potential development of a PoC TB diagnostic tool.

Rational truncation of the original sequences yielded shorter, lower cost molecules that show comparable activity to the original parent sequences. The truncated versions of the aptamers retained the parts of the original (parent) aptamers predicted to play a role in target-binding as can be predicted through secondary structures Truncation of aptamer CSIR 2.11 was effected by secondary structure (2D)-guided methods. The predicted 2D structure for the original sequence of aptamer CSIR 2.11 consists of three stem-loops. Truncation, T2, (77-mer) resulted from cutting out 12 nucleotide bases in the direction 3' to 5'. All the stem-loops, along with their assigned minimum free energy, are all retained in the predicted 2D structures of both truncated versions of the aptamer.

Truncation of aptamer CSIR 2.19 was effected by secondary structure (2D)-guided methods. The predicted 2D structure for the original sequence of aptamer CSIR 2.19 consists of two stem-loops. CSIR 2.19 Truncated (77-mer) resulted from cutting out 12 nucleotide bases in the direction 3' to 5'. Both stem-loops, along with their assigned minimum free energy values, are all retained in the predicted 2D structures of both truncated versions of the aptamer.

Figure 12:
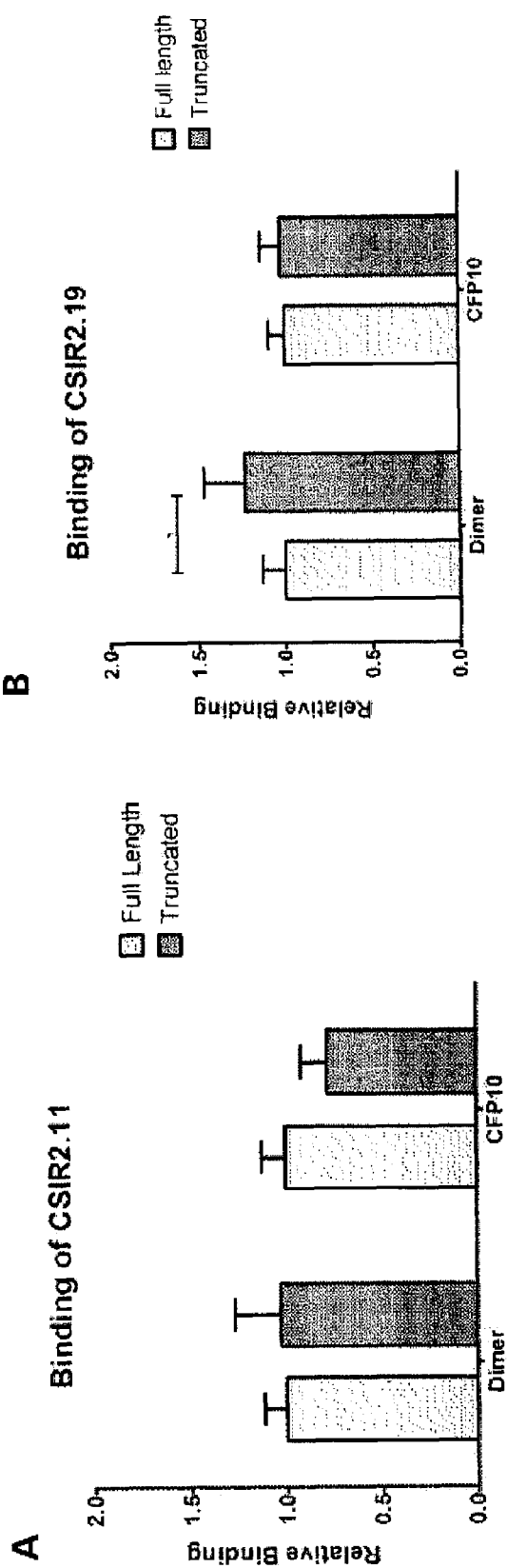
FIG. 12 shows, for Example 10, that truncated aptamers show binding to target proteins, with affinities comparable to those of the parent sequences.

The truncated aptamers show binding to target proteins, with affinities comparable to those of the parent sequences (FIG. 12).

Binding of full length and truncated aptamers to the ESAT-6/CFP-10 dimer and CFP-10 was assessed by ELONA.

FIG. 12A shows apparent binding of CSIR 2.11: the truncated 77-mer bound to the target proteins with affinity values comparable to those of the original 90-mer aptamer.

FIG. 12B shows apparent binding of CSIR 2.19 aptamer: the 77-mer bound to the target proteins with affinity values comparable to those of the original 90-mer aptamer for both ESAT-6/CFP-10 dimer and the CFP-10 monomer. The 77-mer showed slightly higher affinity (*P-value <0.05) for the ESAT-6/CFP-10 dimer than did the 90-mer.

The truncated aptamers can be used in an aptamer-based TB diagnostic tool.

EXAMPLE 11

Figure 13:
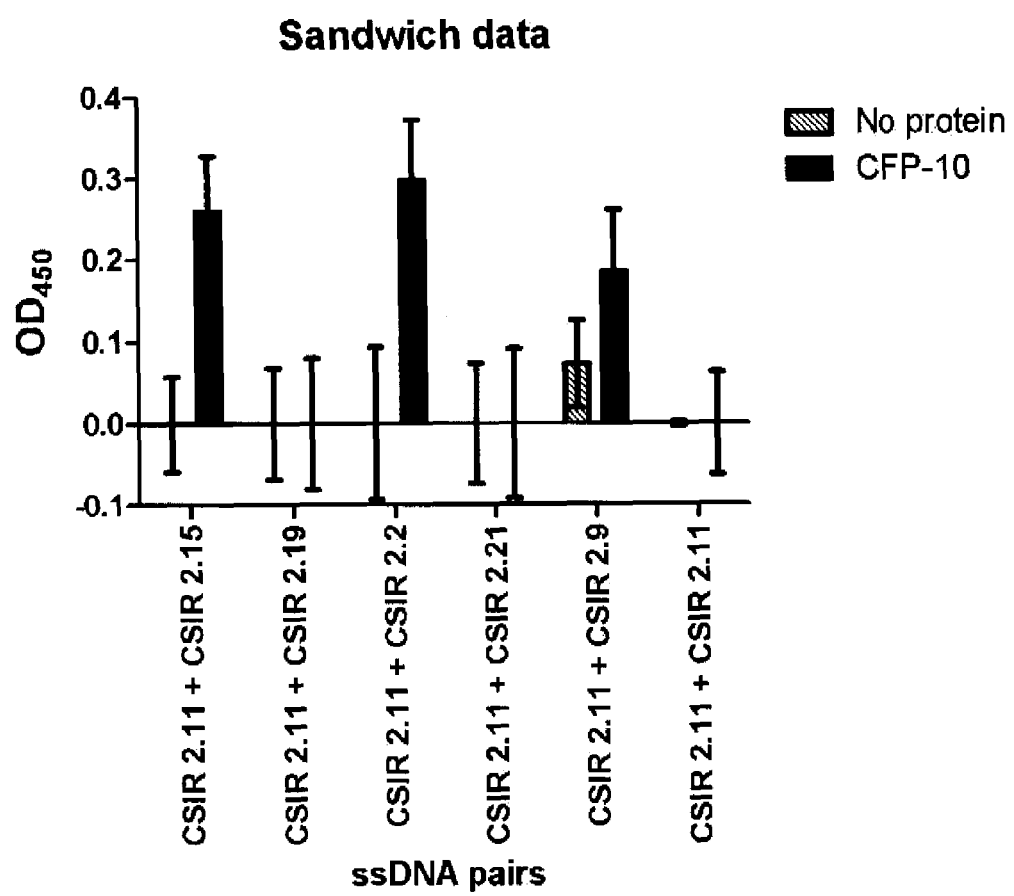
FIG. 13 shows, for Example 11, aptamer sandwich data.

The original full length aptamers can be used in pairs for further use in a diagnostic setting. To test the aptamers in a sandwich ELONA, 96 well micro-titre plates (Corning, Adcock Ingram) were coated with the CSIR2.11 in a 10 mM $NaHCO_3$ buffer pH 8.5 (Sigma) and left overnight at 4° C. The plates were then washed with 1× phosphate buffered saline containing 0.005% Tween 20 (PBS-T) pH7 (Sigma) and blocked with a 5% fat free milk solution for 1 hour at 4° C. The plates were then washed 3 times with a 1×PBS-T after which 500 ng of CFP-10.ESAT-6 heterodimer was added and incubated for 2 hours at room temperature. This was followed by three wash steps with 1×PBS-T and the addition of 150 nM biotinylated aptamer and incubated for a further two hours at room temperature. Following this the plate was washed 3 times with a 1×PBS-T after which a HRP-conjugated streptavidin (diluted 1:10000 in 1×PBS-T) was added and incubated for two hours at 37° C. The plates were then washed four more times with 1×PBS-T, after which a final 3,3',5,5'-tetramethylbenzidine (TMB) detection substrate (Separations) was added. A change in colour to blue, which could be observed with a naked eye, indicated that the aptamers function in a sandwich format. The reaction was stopped with a 2 M sulphuric acid solution (Merck), resulting in a colour change from blue to yellow. The plates were read on the MultiSkan Go plate reader (ThermoScientific, AEC-Amersham) at a wavelength of 450 nm. The pairs were then compared to the no protein pair control using a Student t-test statistical analysis to obtain the p value for significance. Several potential pairs have been identified, as shown in FIG. 13.

EXAMPLE 12

Evaluation of sputum samples using CSIR 2.21 as detection reagent was conducted and compared to the results using CSIR 2.11. A comparison of the ability of CSIR 2.21 and CSIR 2.11 was performed on 28 sputum samples to evaluate the use of CSIR 2.21 in a clinical setting. The comparison was done using an ELONA as in Example 9 using either CSIR 2.11 or CSIR 2.21 as a detection molecule. The comparison is illustrated by FIG. 14 and indicates that both aptamers yielded similar results. As illustrated by FIG. 14, the sensitivity and specificity of CSIR 2.11 and a more specific aptamer, CSIR 2.21, were compared using 28 sputum samples. Using Youden's index, the cut-point for positive samples was set at an $OD_{450}$ of 0.1 and is indicated by the solid line. Data are presented as means±standard deviation of the mean. Samples that gave a positive result when using CSIR 2.21 as a detection molecule are denoted as CSIR 2.21 positive, while negative samples are denoted as CSIR 2.21 negative. Samples that gave a positive result when using CSIR 2.11 as a detection molecule are denoted as CSIR 2.11 positive, while negative samples are denoted CSIR 2.11 negative.

EXAMPLE 13

Figure 15:
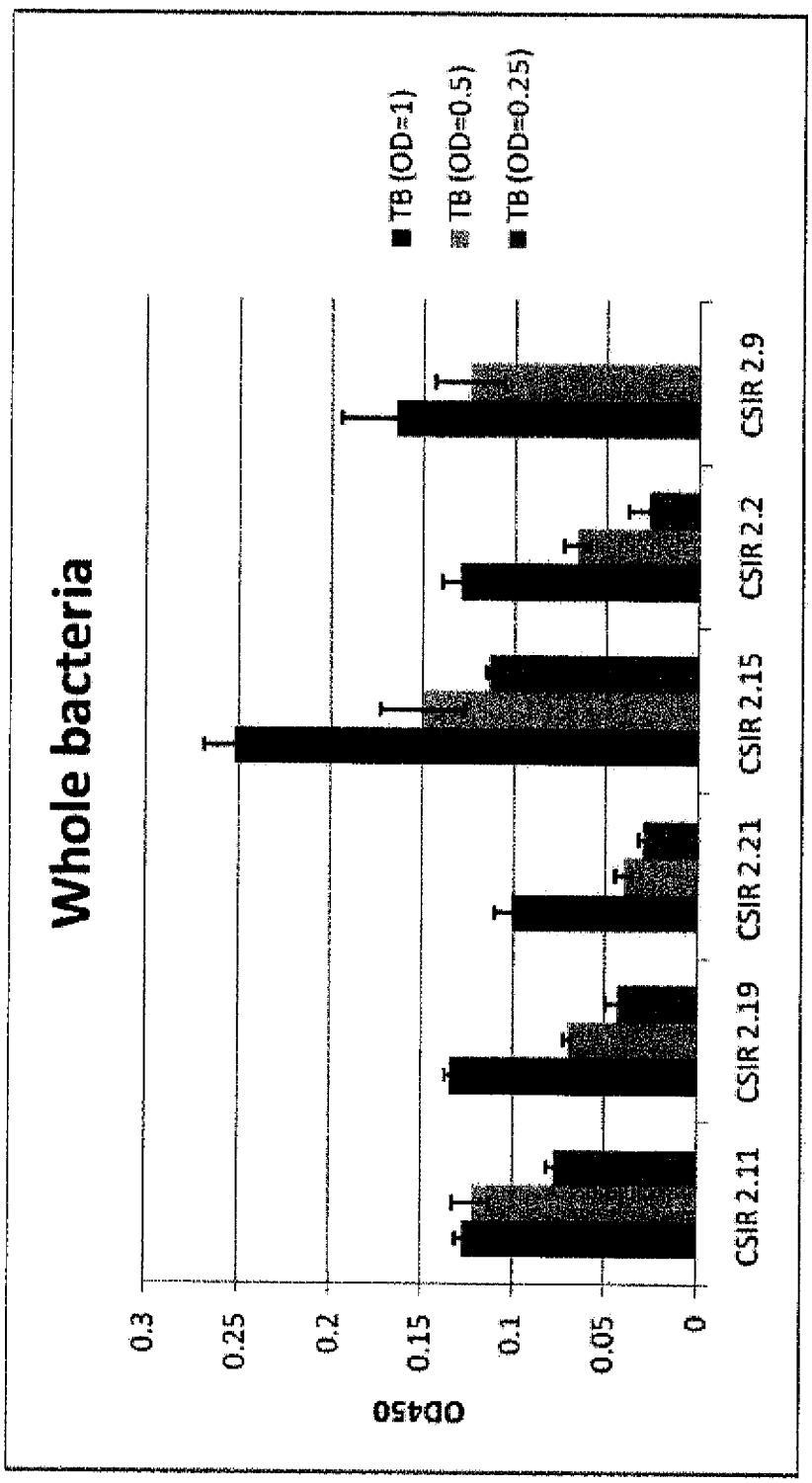
FIG. 15 shows, for Example 13, whole bacteria ELONA.

The aptamers were tested for the detection of whole bacteria, which is useful for diagnostics. To evaluate the aptamers detection of whole bacteria, an ELONA similar to that described in Example 9 was performed, except instead of coating with sputum samples the plate was coated with MTB culture at an $OD_{600}=1$, $OD_{600}=0.5$ and $OD_{600}=0.25$. The whole bacteria ELONA experiments were conducted using the six aptamers: CSIR 2.11, CSIR 2.19, CSIR 2.21, CSIR 2.15, CSIR 2.2 and CSIR 2.9. All six of the aptamers were all able to detect whole bacteria as illustrated in FIG. 15.

While the invention has been described in detail with respect to specific embodiments thereof, it will be appreciated that those skilled in the art, upon attaining an understanding of the foregoing may readily conceive of alterations to, variations of and equivalents to these embodiments. Accordingly, the scope of the present invention should be assessed as that of the appended claims and any equivalents thereto.

The invention claimed is:

1. An oligonucleotide selected from the group comprising SEQ ID NO: 1, SEQ ID NO: 2, SEQ ID NO: 3; SEQ ID NO: 4; SEQ ID NO: 5 and SEQ ID NO: 6, a complementary oligonucleotide thereof, an oligonucleotide being at least 80% homologous thereto, or a pairing of any of the aforementioned.

2. The oligonucleotide of claim 1, which is single stranded.

3. The oligonucleotide of claim 1, which is double stranded.

4. The oligonucleotide of claim 1, which is an aptamer, or a pairing of two aptamers, that binds to a CFP-10.ESAT-6 heterodimer of a Mycobacterium strain.

5. The oligonucleotide of claim 1, which is an aptamer, or a pairing of two aptamers, that binds to a CFP-10 monomer of a *Mycobacterium* strain.

6. The oligonucleotide of claim 4, wherein the *Mycobacterium* strain is the *Mycobacterium tuberculosis* (M.tb) strain.

7. An in vitro method of diagnosing tuberculosis (TB), said method comprising:

(a) contacting a sample taken from an individual suspected to be infected with TB with the oligonucleotide of claim 1 in a CFP-10.ESAT-6 heterodimer binding assay; and (b) determining whether or not the oligonucleotide has bound to a CFP-10.ESAT-6 heterodimer in the sample, with binding of the oligonucleotide to the CFP- 10.ESAT-6 heterodimer thus confirming the presence of the CFP-10.ESAT-6 heterodimer, and hence TB infection in the sample.

8. An in vitro method of diagnosing tuberculosis (TB), said method comprising:
- (a) contacting a sample taken from an individual suspected to be infected with active TB, or latent TB, with the oligonucleotide of claim 1 in a CFP-10 monomer binding assay;

and
- (b) determining whether or not the oligonucleotide has bound to a CFP-10 monomer in the sample, with binding of the oligonucleotide to the CFP-10 monomer thus confirming the presence of the CFP-10 monomer, and hence TB infection in the sample.

9. The method of claim 7, wherein the binding assay is a modified ELISA-type assay, wherein antibodies against the CFP-10.ESAT-6 heterodimer or the CFP-10 monomer are replaced by the oligonucleotide of claim 1.

10. The method of claim 7, wherein the oligonucleotide is that of SEQ ID NO: 3.

11. A diagnostic kit for diagnosing tuberculosis (TB), said kit including:
- (a) a device for taking a sample from an individual suspected to be infected with TB;
- (b) apparatus for applying the method of diagnosing TB according to claim 7;
- (c) the oligonucleotide of claim 1; and
- (d) optionally, a positive control and/or a negative control.

12. The method of claim 8, wherein the binding assay is a modified ELISA-type assay, wherein antibodies against the CFP-10.ESAT-6 heterodimer or the CFP-10 monomer are replaced by the oligonucleotide of claim 1.

13. The method of claim 8, wherein the oligonucleotide is that of SEQ ID NO: 3.

14. A diagnostic kit for diagnosing tuberculosis (TB), said kit including:
- (a) a device for taking a sample from an individual suspected to be infected with TB;
- (b) apparatus for applying the method of diagnosing TB according to claim 8;
- (c) the oligonucleotide of claim 1; and
- (d) optionally, a positive control and/or a negative control.

* * * * *